United States Patent [19]

Maggiolo

[11] 3,938,955
[45] Feb. 17, 1976

[54] NONDESTRUCTIVE METHOD FOR QUICKLY DETERMINING AMOUNT OF LUBRICANT ON TEXTILE

[75] Inventor: Allison Maggiolo, Greensboro, N.C.

[73] Assignees: Glen Raven Mills; Lee H. Peery, both of Glen Raven, N.C. ; part interest to each

[22] Filed: Jan. 20, 1975

[21] Appl. No.: 542,688

[52] U.S. Cl............... 23/230.3; 23/230 R; 73/159; 250/303
[51] Int. Cl.² ................ G01N 33/36; G01N 23/10; G01N 33/28
[58] Field of Search ......... 23/230 R, 253 R, 230 M, 23/230.3; 73/159; 250/303

[56] References Cited
UNITED STATES PATENTS

| | | | |
|---|---|---|---|
| 3,459,506 | 8/1969 | Finucane | 23/230 R |
| 3,560,157 | 2/1971 | Anderson | 23/230 |

OTHER PUBLICATIONS

"Fiber Technology", Textile World, p. 12, July, 1974.

Nelson et al., "Rapid Determination of Bromine–Containing Flame Retardants on Fabrics", Textile Research Journal, June, 1973, pp. 357–361.

*Primary Examiner*—R. E. Serwin
*Attorney, Agent, or Firm*—Parrott, Bell, Seltzer, Park & Gibson

[57] ABSTRACT

A method is disclosed whereby the amount of a lubricant composition such as a spin finish, coning oil, etc. applied to a textile strand may be accurately determined in a matter of seconds or minutes. The method involves applying to a running length textile strand a lubricant composition containing a tracer, winding the lubricated strand into a package, and subjecting the package to nondestructive analysis with an X-ray spectrochemical analyzer to measure the amount of tracer present in the package and to thereby obtain a measurement of the relative amount of lubricant applied to the strand.

16 Claims, No Drawings

NONDESTRUCTIVE METHOD FOR QUICKLY DETERMINING AMOUNT OF LUBRICANT ON TEXTILE

This invention relates generally to a method for determining the amount of a coating composition applied to a strand, such as a textile yarn, and more particularly, relates to a nondestructive testing method whereby the amount of lubricant coating applied to a textile strand may be very rapidly determined.

BACKGROUND OF THE INVENTION

Lubricant compositions such as spin finishes, coning oils, etc. are conventionally applied to textile yarns at various stages during the manufacturing operation to facilitate handling and processing the yarns on textile machinery. It is generally recognized that these lubricants must be applied at carefully controlled levels, since application of improper amounts of lubricant results in various production and quality problems as the yarns are processed into fabrics. For example, when producing knitted fabrics, the application of excessive amounts of lubricant to the knitting yarns may result in a build-up and eventual gumming of the needle latches of the knitting machine, while application of too little lubricant results in excessive needle wear and broken filaments or ends.

Also, it is recognized that it is quite important to apply the lubricant at a uniform level to all of the ends being processed at the respective positions on the textile machinery. Otherwise, when several ends are woven or knitted into a fabric, the variations in lubricant level on the respective ends may become apparent in the fabric as streaking, barre, or uneven dyeing. For example, different levels of lubricant on the several ends fed to a knitting machine may result in variations in tension in the respective yarns which would be readily apparent in the knitted fabric.

Therefore, it is conventional procedure to periodically test the level or percent of lubricant applied to each end being processed to insure that the proper level of lubricant is being applied. This determination of the percent lubricating oil on a yarn has conventionally been made by laboratory extraction methods. In this laboratory procedure, a predetermined length of yarn is taken from a previously wound yarn package, weighed, and placed in a container for a length of time with a heated solvent for the lubricant. After the lubricant has been extracted from the yarn by dissolving in the solvent, the yarn is removed from the container and dried, and the yarn is again weighed to determine the weight percent of oil which was present on the yarn. Obviously this is a time-consuming procedure which takes several hours and requires the dual work of both laboratory technicians and plant personnel. The procedure requires several weighings and measurements and thus provides considerable opportunity for human error. In the several hours of elapsed time between when the sample is taken and when the results are obtained, several thousand dollars worth of yarn containing either too much or too little lubricant may have been produced.

Several proposals have been made for reducing the amount of time required for determining the level of lubricant oil on a yarn. For example, Finucane U.S. Pat. No. 3,459,506 discloses a method wherein the amount of lubricant on the yarn is determined by titration. Another proposed testing procedure disclosed in *Textile World*, July 1974, page 12, employs infrared spectroscopy to obtain a measurement of the amount of oil on the yarn. However, both of these proposed methods still require that a sample of yarn be removed from a previously wound yarn package and subjected to laboratory analysis to determine the amount of lubricant on the yarn. Thus, there is still a significant amount of elapsed time between when the sample is taken and when the results are available, and further, the numerous handling and measuring operations still provide a significant chance for the introduction of human error.

With the foregoing in mind, it is a primary object of this invention to provide a method for determining the amount of a coating composition applied to a strand much more rapidly than has been possible heretofore.

It is another object of this invention to provide a testing method which not only significantly reduces the amount of time required to determine the amount of the coating composition on a strand, but which also provides more reproducible and accurate results than is presently possible by conventional laboratory techniques.

It is a further object of this invention to provide a testing method for determining the amount of lubricant on a textile yarn which may be performed by one individual, and which may be performed in the plant, if desired, rather than in a laboratory.

It is a still further object of this invention to provide a testing method for determining the amount of lubricant coating applied to a textile yarn wherein it is not necessary to remove a length of yarn from a package to obtain a sample but wherein a nondestructive measurement may be made directly to the yarn package, and wherein the measurement may be made in the plant either while the yarn is still being wound into a package or after completion of winding and doffing of the package, and wherein the results of the measurement are available almost immediately so that corrective measures may be taken if an improper amount of lubricant is being applied.

SUMMARY OF THE INVENTION

The above and other objects are achieved in accordance with this invention by employing a method of tracer analysis to determine the amount of lubricant composition applied to a textile yarn.

More particularly, in accordance with this invention the lubricant composition which is applied to the yarn contains a tracer which is capable of being later quantitatively measured. The lubricated yarn is wound into a package and the package is subjected to tracer analysis to quantitatively measure the amount of tracer present in the yarn package. The level of tracer measured is a function of the amount of lubricant present on the yarn, and thus the weight percent of lubricant present on the yarn may be readily determined.

Preferably, a type of radiation analysis such as X-ray spectrographic analysis is employed, which permits rapidly and accurately measuring, in a nondestructive manner, the amount of tracer in the yarn package.

X-ray spectrographic analysis has been applied in various manners and in various areas of technology in both qualitative and quantitative analysis. For example, X-ray spectrographic procedures have been employed for analyzing the composition of metals and alloys, and for measuring coating thicknesses on a substrate, such as the thickness of an electroplated layer or the thickness of a paint coating. Such procedures have also been employed for measuring coatings on fabrics. For example, an article by K. H. Nelson and W. D. Brown in the June 1973 *Textile Research Journal* (page 357) discloses a method wherein X-ray spectrographic analysis is employed for measuring bromine containing flame retardant coatings on fabrics.

However, none of these known procedures employing X-ray spectrographic analysis have been proposed for use in determining the amount of a lubricant coating on an individual textile strand, nor would application of such known procedures be practical or possible due to one or more of the following considerations:

1. The known procedures require the presence in the sample being tested of a considerable amount of an element capable of being quantitatively analyzed by X-ray spectrographic analysis. A textile yarn is too small to carry the necessary quantity of tracer element needed for detection by X-ray spectrographic analysis;

2. Extensive and delicate sample preparation is involved;

3. It is usually necessary to know the weight of the sample being analyzed;

4. The testing procedure usually involve destructive testing of the sample; and

5. The testing methods and computations required for obtaining quantitative data are complicated and involved.

The testing method in accordance with this invention requires essentially no sample preparation and may be performed directly on a yarn package in the plant, either while the package is still running on the textile winding machine or immediately after doffing.

In the known methods where a coating thickness is determined by X-ray spectrography, the coating or layer being measured has a considerable thickness and contains a relatively high proportion of a quantitatively measurable element. At the relatively low levels at which yarn lubricants such as spin finishes, coning oils, etc. are conventionally applied, which is generally not more than about 6 to 8 percent by weight based upon the dry yarn and often less than one percent by weight, the amount of tracer which can be applied to a single end of yarn is too low for being quantitatively measured by X-ray spectrochemical analysis. However, the method of the present invention is able to overcome this problem by subjecting the entire yarn package to analysis and measuring the combined effect of the tracer present in a number of overlying and adjacent portions of the wound yarn in the package. This invention thus eliminates the need for unreeling a predetermined length of yarn from the package in order to obtain a sample for analysis as has been the conventional practice in the standard laboratory methods. Moreover, since in the method of this invention the yarn package forms the sample and the analysis performed thereon is nondestructive, no yarn is wasted from the package. Further, the probe used for measuring the amount of tracer reads down into the depth of the package rather than only at the surface thereof and the reading obtained is thus an average over most of the length of the yarn in the package rather than a reading based only on the outer few yards of yarn on the package as occurs in standard laboratory procedures.

The testing method in accordance with this invention is independent of the weight of the yarn package being measured and this contributes considerably to the speed and accuracy of this method. It is only necessary that the yarn package which is subjected to analysis be of sufficient width and thickness so that when the package is positioned in proximity to the probe of the analysis instrument, the entire field of the probe is filled by the yarn. Thus, a sample of "infinite mass" is presented to the probe.

In order that the yarn lubricant may be measured by the present method, it is necessary that the lubricant contain a tracer capable of quantitative analysis on a suitable instrument such as an X-ray spectrochemical analyzer. The tracer employed may either be a chemical element already present in the lubricant or may be an element present in an additive compound which is mixed with the lubricant. If the tracer is contained in an additive compound, the additive must be compatible with the lubricant so as to remain in a stable and homogenous admixture with the lubricant. This is necessary to insure application of the tracer to the yarn at a uniform concentration during application thereof. It is also important that the additive compound will not undesirably alter the lubricant properties of the lubricant. Further, the additive should remain stable under the conditions of heat to which it may be later subjected. Otherwise, the additive compound might break down into harmful acids or form harmful deposits on the machinery under subsequent processing conditions.

DESCRIPTION OF PREFERRED EMBODIMENT

The preferred method of nondestructive tracer analysis is carried out on a commercially available instrument known as an X-ray spectrochemical analyzer. This is a lightweight portable instrument consisting of a probe and an electronic console. The probe contains a low level radioisotopic source which emits radiation through an opening or window in the probe housing in the direction of the sample being tested. Radiation striking the sample causes emission of characteristic X-rays from the various elements present in the sample. Some of these secondary X-rays pass from the sample back into the probe through the opening therein and enter a detector located under the source, where voltage pulses proportional in magnitude to the X-rays are generated. The pulses are sorted and those characteristic of the particular element being measured are counted for a predetermined length of time ranging from a few seconds up to about a minute. The number of pulses or "counts" detected during the counting period for the particular element are displayed on the console.

One suitable instrument for this purpose is the Panalyser-4000, made by Panametrics of Waltham, Mass. This instrument can be used to measure a total of 67 elements out of a known total of 104. Elements which cannot be measured are those lighter than silicon or heavier than uranium, and certain other inert or unstable elements.

In order to measure the amount of lubricant on the yarn employing this instrument, it is necessary that the lubricant contain a tracer element capable of being measured by the instrument. If a silicone lubricant is employed, the lubricant may be measured directly by measuring the amount of silicon in the lubricant coating on the yarn. If conventional natural oils of animal, vegetable, or mineral origin are used as the lubricant however, it is necessary that an additive compound containing a tracer element measurable by the X-ray spectrochemical analyzer be mixed with the lubricant oil. This tracer compound may contain silicon, iodine, chlorine, etc. However, it is most convenient for practical reasons of cost, availability, stability, and compatability with the lubricant oil to employ brominated organic compounds as the tracer compound.

Specifically, the organic bromine tracer compounds which were found to be most effective for use in this method are relatively non-volatile heat stable hydrophobic unreactive paraffinic and aromatic brominated compounds such as the following: tetrabromoethylene, hexabromobenzene, penta-bromoethane, brominated fatty esters, tetrabromobisphenol-A, tris-bromomethyl ethyl alcohol, pentabromobenzenes such as Formula (1),

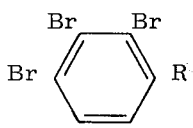

Formula (1)

where R can be alkyl, OH, OCH$_3$, etc.

and multibromobenzenes such as Formula (2).

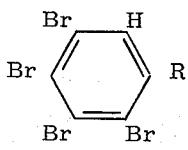

Formula (2)

where R can be H, alkyl, OH, OCH$_3$, etc.

These compounds have been found to form stable homogeneous mixtures with the animal, vegetable, or mineral oils conventionally employed as yarn lubricants and to remain stable during subsequent processing, texturizing, finishing, etc.

It is most important that the brominated organic compound remain stable throughout the processing operations to which the yarn is subjected, since unstable compounds might break down and form harmful acids or deposits on the processing machinery. As is well known, during conventional texturizing operations, yarns are heated by passing through heated chambers or across heated rolls or pins. Brominated compounds which are unstable at high temperatures might decompose when subjected to these conditions and form hydrobromic acid. In this regard, it has been found, at least with respect to aliphatic compounds, that for desirable heat stability properties, the brominated organic compounds employed are preferably those which do not have a hydrogen atom on the carbons which are alpha (attached) to the bromine-bearing carbon atoms. Compounds having a hydrogen atom located on a carbon alpha to a bromine-bearing carbon atom tend to split off hydrobromic acid at elevated temperatures.

It is also important that the additive compound does not undesirably affect or alter the lubricant properties of the oil to which it is added. The above-noted classes of brominated organic compounds, when mixed in limited amounts with the lubricant oils, have been found to be quite compatible with the lubricant oils without undesirably altering the lubricating properties thereof.

The tracer compound is preferably combined with the lubricant oil at a concentration of up to about five percent by weight, and preferably within the range of about one-half to three percent by weight. The bromine compound employed preferably contains between about 30 to 70 percent by weight of bromine. It will be apparent that if the bromine compound contains a higher percentage of bromine, then a lower amount of compound may be added to the lubricant. As noted earlier, the yarn lubricant is conventionally applied to the yarn at levels ranging from less than one percent up to about six to eight percent by weight on the yarn. From these figures, it will be readily seen that a very low concentration of bromine of no more than about 0.20 to 0.30 percent by weight is present on the yarn. Usually this concentration is quite lower, in the order of 0.02 percent or less. At this very low concentration, the X-ray spectrochemical analyzer is incapable of distinguishing the bromine counts from the background radiation on a single end of the yarn. However, by positioning a yarn package against the probe and measuring the combined effects of a large number of adjacent and overlying portions of the yarn, a sufficient concentration of bromine is present to provide an accurate and reproducible reading.

In performing a measurement by the method of this invention, the probe of the analyzer is positioned in close proximity with a yarn package and a count of the number of characteristic X-rays of the selected element is made for a predetermined measurement time, usually ranging from about fifteen seconds to about one minute. This measurement may be accomplished by placing a wound yarn package against the probe of the instrument, or by positioning the probe close to the surface of a package still running on the textile winding machine.

In order to obtain consistent readings from one sample to another, and to eliminate the need for individually weighing each sample, the yarn package should be of "infinite mass" relative to the field of the probe of the analyzer. The term infinite mass sample, as used herein, means a sample which is of a size or mass equal to or greater than the maximum field or scope of the probe. For any given probe, there is a certain maximum limit to its field, and it cannot distinguish or read anything beyond this limit. Thus, regardless of the size or mass of the sample being measured, so long as the sample is sufficiently large to fill the field of the probe, the reading obtained will be the same, since the probe will "see" only that portion of the sample which is within its field.

In the case of the Panalyser-4000 instrument employed herein, it was found that the yarn package should have a minimum thickness of about one inch of yarn measured radially from the outer periphery of the core to the outer periphery of the yarn package. This insures that when the probe is positioned against the yarn package, the probe "sees" a constant portion of each of the various yarn packages measured. The minimum thickness yarn package to insure an infinite mass sample may be readily determined experimentally for other types of analysis instruments and probes.

In order to determine the weight percent of lubricant on the yarn from the number of counts read by the analyzer, reference is conveniently made to a calibration chart or graph. In making the calibration graph, duplicate analyses are performed on a number of samples both by standard laboratory procedures, such as the conventional extraction technique, and by the X-ray spectrochemical analysis of this invention. The weight percent of oil on yarn obtained by standard laboratory analysis for each sample is plotted as ordinate against the corresponding number of counts obtained by X-ray spectrochemical analysis as abscissa. This plot produces an essentially linear relationship over the concentration ranges normally encountered. Since the half life of the radioisotopic source in the probe is quite long, over 400 years, the calibration curve is stable and does not require periodic recalibration.

In many instances, it is not necessary to know the actual percentage of oil being applied, but only whether the lubricant level is within certain limits. Thus, the method of this invention may suitably be employed merely to determine relative amounts of lubricant oil without referring to a calibration chart, as for example, by ascertaining directly whether the digital readout of the instrument is within arbitrary limits.

In actual comparative tests performed on a number of yarn packages coated with various amounts of lubricant, the method of this invention was found to provide significantly more reproducible and accurate results than the conventional laboratory extraction method of measurement.

That which is claimed is:

1. A nondestructive testing method for quickly measuring the amount of a coating applied to a strand, said method employing a radiation analysis instrument having a predetermined field and being adapted for quantitatively measuring a tracer, said method comprising applying to a running length strand a coating composition containing a tracer, winding the coated strand into a package of infinite mass relative to the field of the analysis instrument, and subjecting the package to analysis by the instrument to obtain a reading of the amount of tracer within the field of the instrument, which reading provides a relative indication of the amount of coating applied to the individual strand.

2. A method according to claim 1 wherein the step of subjecting the package to analysis is performed on the package after completion of winding of the strand thereon.

3. A method according to claim 1 wherein the step of subjecting the package to analysis is performed on the package during winding of the strand thereon.

4. A method according to claim 1 wherein the radiation analysis instrument is a nondestructive X-ray spectrochemical analyzer having a probe with a predetermined field, and wherein the step of subjecting the package to analysis by the instrument comprises positioning the package in such relation to the probe of the X-ray spectrochemical analyzer as to fill the field thereof, and thereafter obtaining a measurement on the analyzer of the amount of tracer within the field of the probe.

5. A method according to claim 1 comprising the additional step of comparing the measured amount of tracer with a calibration standard to thereby determine the actual amount coating applied to the individual strand.

6. A method according to claim 1 wherein the tracer-containing coating composition applied to the strand comprises a silicone lubricant.

7. A method according to claim 1 wherein the tracer-containing coating composition applied to the strand comprises a natural lubricant oil of animal, vegetable, or mineral origin having intimately admixed therewith a compatible heat stable organic halogen tracer compound.

8. A nondestructive testing method for quickly measuring the amount of a lubricant coating applied to a textile strand and wherein the coating contains a tracer quantitatively measurable by an X-ray spectrochemical analyzer having a predetermined field, said method comprising preparing a sample of the coated textile strand which is of infinite mass relative to the analyzer, positioning the sample within the field of the analyzer, and obtaining a reading from the analyzer of the amount of tracer on the portion of the sample within the field thereof to thereby obtain a relative indication of the amount of coating applied to the individual strand.

9. A method according to claim 8 wherein the step of preparing a sample of the coated strand which is of infinite mass relative to the field of the analyzer comprises winding the strand into a package of a width and thickness sufficient to fill the field of the analyzer.

10. A nondestructive testing method for quickly measuring the amount of lubricant applied to a textile strand said method employing an X-ray spectrochemical analyzer having a probe with a predetermined field and being adapted for measuring the amount of a predetermined element located within the field of the probe, said method comprising applying to a running length textile strand a lubricant composition containing a predetermined tracer element, winding the lubricated strand into a package of a width and thickness sufficient to fill the field of the probe, positioning the package in close proximity to the probe, and measuring with the analyzer the amount of the predetermined tracer element present in the portion of the package within the field of the probe to thereby obtain a reading proportional to the amount of lubricant applied to the individual strand.

11. A method according to claim 10 wherein the lubricant composition is applied to the strand at a level of not more than about 8 percent by weight based upon the dry yarn.

12. A method according to claim 10 wherein the lubricant composition applied to the textile strand has a concentration of tracer element below the level which could be measured by the analyzer on a single end of the textile strand.

13. A method according to claim 10 wherein the lubricant composition applied to the textile strand has a tracer element concentration of no more than about 0.30 percent by weight.

14. A method according to claim 10 wherein the lubricant composition applied to the textile strand comprises a natural oil of animal, vegetable, or mineral origin having intimately admixed therewith up to about 5 percent by weight of a compatible heat stable brominated organic tracer compound.

15. A method according to claim 14 wherein the brominated organic tracer compound comprises a hydrophobic unreactive paraffinic brominated compound.

16. A method according to claim 14 wherein the brominated organic tracer compound comprises an aromatic brominated compound.

* * * * *

UNITED STATES PATENT OFFICE
CERTIFICATE OF CORRECTION

PATENT NO. : 3,938,955
DATED : February 17, 1976
INVENTOR(S) : Allison Maggiolo

It is certified that error appears in the above-identified patent and that said Letters Patent are hereby corrected as shown below:

In the Title - after "Textile" insert --Strands--;

Column 8, Line 13, after "the" insert --field of the--.

Signed and Sealed this

Thirty-first Day of August 1976

[SEAL]

Attest:

RUTH C. MASON
Attesting Officer

C. MARSHALL DANN
Commissioner of Patents and Trademarks